United States Patent [19]

Yamaguchi et al.

[11] Patent Number: 4,859,688
[45] Date of Patent: Aug. 22, 1989

[54] METHOD FOR THE TREATMENT AND PREVENTION OF ARTERIOSCLEROSIS WITH NITROPHENYL SUBSTITUTED DIHYDROPYRIDINES

[75] Inventors: Isamu Yamaguchi, Ibaraki; Jiro Hirosumi, Tokyo, both of Japan

[73] Assignee: Fujisawa Pharmaceutical Co., Ltd., Osaka, Japan

[21] Appl. No.: 31,746

[22] Filed: Mar. 30, 1987

Related U.S. Application Data

[63] Continuation-in-part of Ser. No. 801,842, Nov. 26, 1985, abandoned.

[30] Foreign Application Priority Data

Dec. 10, 1984 [GB] United Kingdom ............... 8431119

[51] Int. Cl.$^4$ ............................................. A61K 31/44
[52] U.S. Cl. ................................... 514/344; 514/824
[58] Field of Search ........................................ 514/344

[56] References Cited

U.S. PATENT DOCUMENTS 4,150,119 4/1979 Lince Lalinde ............... 424/144
4,307,103 12/1981 Sato et al. ........................ 514/344
4,338,322 6/1982 Sato ................................... 514/344
4,442,100 4/1984 Meyer et al. ..................... 514/821

FOREIGN PATENT DOCUMENTS 3307422 9/1984 Fed. Rep. of Germany ...... 514/344

*Primary Examiner*—Douglas W. Robinson
*Assistant Examiner*—Joseph A. Lipovsky
*Attorney, Agent, or Firm*—Oblon, Spivak, McClelland, Maier & Neustadt

[57] ABSTRACT

The invention relates to a novel method for the treatment and prevention of arteriosclerosis, which comprises administering, as an active ingredient, a dihydropyridine compound of the formula:

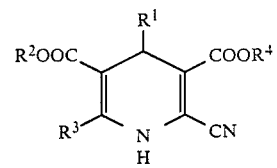

in which $R^1$ is nitrophenyl and $R^2$, $R^3$ and $R^4$ are each lower alkyl, or pharmaceutically acceptable salts thereof.

2 Claims, No Drawings

METHOD FOR THE TREATMENT AND PREVENTION OF ARTERIOSCLEROSIS WITH NITROPHENYL SUBSTITUTED DIHYDROPYRIDINES

This application is a continuation-in-part of Application Ser. No. 801,842, filed Nov. 26, 1985, now abandoned.

The present invention relates to a novel method for the treatment and prevention of arteriosclerosis.

More particularly, it relates to a novel method for the treatment and prevention of arteriosclerosis, which comprises administering, as an active ingredient, a dihydropyridine compound of the formula:

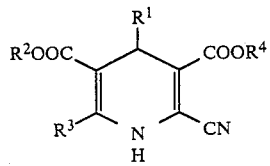

in which
$R^1$ is nitrophenyl and
$R^2$, $R^3$ and $R^4$ are each lower alkyl, or pharmaceutically acceptable salts thereof.

Suitable pharmaceutically acceptable salts of the compound (I) are conventional non-toxic salts and may include an acid addition salt such as an organic acid addition salt (e.g. acetate, trifluoroacetate, maleate, tartarate, methanesulfonate, benzenesulfonate, formate, toluenesulfonate, etc.), an inorganic acid addition salt (e.g. hydrochloride, hydrobromide, hydroiodide, sulfate, nitrate, phosphate, etc.), or a salt with an acidic amino acid (e.g. aspartic acid, glutamic acid, etc.), and the like.

The dihydropyridine compound (I) to be used in the present invention is known and described in some publications, for example, the British Patent No. 2,036,722. Further, as to the pharmacological property of the dihydropyridine compound (I), it is also publicly known that the compound (I) possesses vasodilating activity.

As a result of an extensive study, the inventors of the present invention have found that the dihydropyridine compound (I) or pharmaceutically acceptable salts thereof possess an anti-arteriosclerotic activity in addition to the known vasodilating activity, and have succeeded in providing the present invention.

The anti-arteriosclerotic activity of the dihydropyridine compound (I) or pharmaceutically acceptable salts thereof is a novel pharmacological property, which can be said to be pharmacologically different from the vasodilating activity as described in the prior art mentioned above.

Accordingly, the object of the present invention is to provide a novel method for the treatment and prevention of arteriosclerosis in mammals, which comprises administering the compound (I) or a pharmaceutically acceptable salt thereof to said mammal.

As such arteriosclerosis, there may be exemplified atherosclerosis, hypertensive arteriosclerosis, Monckeberg's arteriosclerosis, hyperplastic arteriosclerosis, and the like, and the dihydropyridine compound (I) or pharmaceutically acceptable salts thereof are useful for the treatment and prevention of such diseases and further cardiovascular disorders such as angina pectoris, myocardial infarction, etc., hypertension, apoplexy, intermittent claudication, gangrene, arteriosclerosis of the aorta, arteriosclerotic aneurysms and arteriosclerosis of the renal arteries, and the like, induced thereby.

With regard to the dihydropyridine compound (I), suitable examples and illustrations of the definitions for $R^1$, $R^2$, $R^3$ and $R^4$ are explained in detail as follows.

Suitable example of "nitrophenyl" for $R^1$ may include 2-nitrophenyl, 3-nitrophenyl and 4-nitrophenyl, and the preferred one is 3-nitrophenyl.

Suitable example of "lower alkyl" for $R^2$, $R^3$ and $R^4$ may include alkyl having 1 to 6 carbon atoms such as methyl, ethyl, propyl, isopropyl, butyl, isobutyl, sec-butyl, pentyl, isopentyl, neopentyl, 1- or 2-methylbutyl, hexyl, and the like, in which the preferred one is $C^{1}$-$C^{4}$alkyl, and the most preferred one for $R^2$ is isopropyl and the most preferred examples for $R^3$ and $R^4$ are each methyl.

The anti-arteriosclerotic composition used int he present invention can be administered orally or parenterally to mammals in a conventional pharmaceutical form such as capsules, micro-capsules, tablets, granules, powders, troches, pills, ointments, suppositories, injection solutions, syrups, and the like.

The pharmaceutical composition of the present invention can be produced by the established procedures using various organic or inorganic carriers, which are conventional for pharmaceutical purpose, such as excipient (e.g. sucrose, starch, mannit, sorbit, lactose, glucose, cellulose, talc, calcium phosphate, calcium carbonate, etc.), binding agent (e.g. cellulose, methyl cellulose, hydroxypropylmethyl cellulose, polypropylpyrrolidone, gelatin, gum arabic, polyethylene glycol, sucrose, starch, etc.), disintegrator (e.g. starch, carboxymethyl cellulose, hydroxypropyl starch, sodium bicarbonate, calcium phosphate, calcium citrate, etc.), lubricant (e.g. magnesium stearate, aerosil, talc, sodium laurylsulfate, etc.), flavoring agent (e.g. citric acid, mentol, glycine, orange powders, etc.), preservative (e.g. sodium benzoate, sodium bisulfite, methylparaben, propylparaben,etc.), stabilizer (e.g. citric acid, sodium citrate, acetic acid, etc.), suspending agent (e.g. methyl cellulose, polyvinylpyrrolidone, alminum stearate, etc.), dispersing agent (e.g. hydroxypropylmethyl cellulose, etc.), diluting agent (e.g. water, etc.), base wax (e.g. cacao butter, white petrolatum, polyethylene glycol, etc.).

While the dosage of the active ingredient of the compound (I) is varied depending on various factors such as weight and/or age of patients and/or stages of the diseases, and further the kind of administration routes, it is administered in general by oral route at the daily dose level of 0.5 mg to 1000 mg, preferably 1 mg to 500 mg. An effective single dose can be selected from the range of 0.01 mg/kg to 20 mg/kg, preferably 0.05 mg/kg to 2 mg/kg of the patients.

For the purpose of showing the utility of the dihydropyridine compound (I) or pharmaceutically acceptable salts thereof used for the anti-arteriosclerotic composition used in the present invention, pharmacological test data of this compound are shown in the following.

Test 1:

Effect on arteriosclerotic change induced by cuff in rabbit carotid artery

Test Method

The arteriosclerosis which is characterized by intimal thickening was made in rabbits (about 2 kg weight) by the following method.

Under pentobarbital anesthesia, the left carotid artery was isolated from the surrounding tissue, put into a cuff (1.5 cm long PE-280) through a longitudinal slit and was returned to the place as it was. Then, the wound was sutured and the rabbits were recovered and fed with normal diet. Three weeks after surgery, the rabbits were anesthetized with pentobarbital and sections were taken of the carotid artery. The part of the artery covered by a cuff was examined under microscope for the arteriosclerotic index which was rated at 0, 1, 2 and 3 according to the degree of intimal thickening. For each rabbit, about 30 transverse sections were taken at random, and the mean arteriosclerotic index was used for the determination of the effect. Test Compound was suspended in 0.5% methyl cellulose and injected intramuscularly for 5 days each week beginning from one day after cuff treatment to one day before sacrifice. The injection volume was adjusted to 0.5 ml/kg.

Test Compound

Isopropyl ester of 6-cyano-5-methoxycarbonyl-2-methyl-4-(3-nitrophenyl)-1,4-dihydropyridine-3-carboxylic acid (hereinafter referred to as Dihydropyridine Compound A)

Test Results

| Dose of Test Compound (mg/kg) | Arteriosclerotic Index |
|---|---|
| 1.0 | 0.85 ± 0.16 |
| 10 | 0.61 ± 0.21 |
| Control | 1.88 ± 0.18 |

TEST 2:

Induction of intimal thickening of rabbit carotid artery by polyethylene cuff treatment

Test Method

Eight (8) male Japanese white rabbits weighing about 2 kg were used for each test group. The rabbits were anesthetized with 12.5 mg/kg petobarbital and the left carotid artery was isolated with care not to injure the surrounding tissues. A polyethylene cuff (1.5 cm long PE280, inner diameter 2.15 mm, outer diameter 3.25 mm, made by Becton Dickinson & Co.) was placed around the artery according to the technique reported by Rosnowski et al. (CR. Acad, Sci. Paris, 271 (1970) 1467). The rabbits were maintained for 3 weeks on normal diet and water. Test Compounds and vehicles were given intramuscularly once a day starting from the day of cuff-placement. At the end of the 3rd week, the rabbits were heparinized (500 U, i.v.), and the artery was removed, washed free of blood with saline, fixed by immersion in 10% formalin and divided into 8 cross segments about 2 mm long. The segments were embedded in paraffin and cut into transverse sections. These sections were stained with orcein. About 70 transverse sections were prepared from each artery and used for the quantitation of the Arteriosclerotic Index.

Quantitation of Arteriosclerotic Index

The arterial sections were observed by light microscopy and the Arteriosclerotic Index was scored as follows.

0: No thickening.

1: slight hyperplasia in the subendothelial space with intima-media ratio of about 1/10.

2: several layers of cells in the subendothelial space with intima-media ratio of about 1/5, or parts of the subendothelial space with more hyperplasia.

3: sever hyperplasia throughout the subendothelial space with intima-media ratio of more than 1/3.

Test Compounds

1. Dihydropyridine Compound A
2. Dimethyl ester of 2,6-dimethyl-4-(2-nitrophenyl)-1,4-dihydropyridine-3,5-dicarboxylic acid (hereinafter referred to as Nifedipine)

Test Results

The values show the Arteriosclerotic Index (mean ± standard error).

| Test Compounds | Dose (mg/kg) | | |
|---|---|---|---|
| | 0 (control) | 1 | 10 |
| Dihydropyridine Compound A | 2.01 ± 0.20 | 0.85 ± 0.15 | 0.61 ± 0.19 |
| Nifedipine | 1.99 ± 0.26 | 0.94 ± 0.21 | 1.19 ± 0.26 |

TEST 3:

Inhibition of migration of smooth muscle cell (SMC)

Test Methods

Preparation of inflammatory exudates from zymosan-activated air pouch in rats:

Inflammatory exudates were obtained according to the method of Konno and Tsurufuji [Br. J. Pharmacol., 80 (1983) 269]. Seven-week-old male Wistar rats were injected subcutaneously with 12 ml of air on the back to make a pouch. Twenty-four hours later 6 ml of 1.6% (W/V) zymosan suspension in 0.5% (W/V) methyl cellulose solution in saline was injected into the pouch to induce inflammation. After 3 days the inflammatory exudates were collected with pipets and centrifuged for 15 minutes at 2,000 G. The supernatant was stored at −80° C. until used.

Culture of rat aortic smooth muscle cells (SMC):

Rat aortic SMC were isolated and cultured by the method of Ross [J. Cell Biol. 50 (1971) 172]. Briefly, aortic SMC were isolated from medial explants of thoracic aorta of seven-week-old male Wistar rats and cultured in Eagle's minimum essential medium supplemented with 10% calf serum, penicillin G (100 μg/ml) and dihydrostreptomycin sulfate (100 μg/ml). After 7–10 days, the cells began to migrate from the explants. When the cells became confluent, they were subcultured in the same medium. These cells exhibited the characteristic "hill and valley" morphology of vascular SMC in culture. Cells under passage 10 were used in this study.

Migration of SMC:

Migration of SMC was examined in modified Boyden chambers using a filter membrane with pores of 8 μm diameter [Atherosclerosis, 43 (1982) 143]. The above mentioned cells in 75—cm² Falcon flasks were treated with a solution of 0.008% trypsin - 0.01% ethylenediaminetetraacetic acid for 30 seconds at room temperature. After removing this solution, the cells in the flasks were rinsed twice with calcium-, magnesium-free phosphate buffer (pH 7.2) and incubated for 5-10 minutes at 37° C. The obtained cells were suspended at a concentration of $5 \times 10^5$ cells per 1 ml of Eagle's minimum essential medium supplemented with 5% calf serum. One-tenth (0.1) ml of the Test Compound solution or vehicle (1% ethanol in the culture medium for each Test Compound) was added to 0.9 ml of the cell suspension ($5 \times 10^5$ cells/ml) placed in the upper compartment of the chamber. The lower compartment contained 5% zymosan-activated air pouch exudates in culture medium supplemented with 5% calf serum. After 8 hours incubation at 37° C. in an atmosphere of 95% air and 5% $CO_2$, the filters were removed, fixed in 95% ethanol and stained with hematoxylin. SMC migration was quantitated microscopically by counting the number of cells that migrated into the filter to a depth of 30μm. Ten high-power fields (HPF, x 400) were examined for each filter and cell migration was expressed as cells per 10 HPF.

Test Compounds

1. Dihydropyridine Compound A
2. Nifedipine

Test Results

| Test Compounds | $IC_{50}$ (M) |
|---|---|
| Dihydropyridine Compound A | $3.3 \times 10^{-11}$ |
| Nifedipine | $1.7 \times 10^{-10}$ |

TEST 4:

Inhibition of vitamin-$D_3$-induced rise in Ca content of the thoracic aorta

Test Method

Male Fischer rats weighing about 150g were used for each test. They were divided into 5 to 6 groups of 10 animals; one served as control, and the others as tested groups. The tested groups were given orally 10μg/kg 1-α hydroxyvitamin $D_3$ (corn oil suspension, 0.5ml/150g) once a day for 2 weeks. Control group rats were given the same volume of Vehicle (corn oil). Test Compounds (corn oil suspension, 0.5ml/150g) were administered per os twice a day, starting on the day of 1-α hydroxyvitamin $D_3$ dosing. Placebo group was given the same volume of corn oil.

The thoracic aorta was removed from the rats treated as above, cleaned of surrounding tissues, and dried at 110° C. for 6 hours to obtain dry weight. The aorta was dissolved by boiling in the mixture of acids (perchloric acid : sulfuric acid : nitric acid : water = 4:1:1:1). The obtained solution was used for the determination of calcium. Calcium was measured with an atomic absorption spectrophotometer (Model A-1800, made by Hitachi Co., Ltd. Japan).

Test Compounds

1. Dihydropyridine Compound A
2. Nifedipine

Test Results

Figures in the following Table represent means± standard error (% of control).

| Test Compounds | Dose (mg/kg) | | | | | $ED_{50}$ (mg/kg) |
|---|---|---|---|---|---|---|
| | 0 | 0.1 | 1 | 10 | 100 | |
| Dihydropyridine Compound A | 100 | 94 ± 9 | 57 ± 13 | 27 ± 6 | 8 ± 3 % | 2.2 |
| Nifedipine | 100 | — | 93 ± 15 | 58 ± 15 | 30 ± 10 % | 23.2 |

The present invention is explained according to the following Examples.

EXAMPLE 1

Dihydropyridine Compound A: 100 g
Hydroxypropylmethyl Cellulose: 500 g

Dihydropyridine Compound A was dissolved in anhydrous ethanol (5 liters) and then hydroxypropylmethyl cellulose was added thereto to prepare a suspension. Then the organic solvent was removed under reduced pressure to give solid dispersion composition.

EXAMPLE 2

Dihydropyridine Compound A: 100 g
Hydroxypropylmethyl Cellulose: 500 g
Sucrose: 9.4 kg To a suspension of Dihydropyridine Compound A and hydroxypropylmethyl cellulose in anhydrous ethanol (5 liters) was added sucrose and the resultant mixture was stirred. Then the organic solvent was removed under reduced pressure to give solid dispersion composition. This composition was converted into fine granules by a conventional method.

EXAMPLE 3

Dihydropyridine Compound A: 100 g
Hydroxypropylmethyl Cellulose: 500 g
Lactose: 6.87 kg
Low-substituted Hydroxypropyl-Cellulose 1.5 kg
Magnesium Stearate: 30 g To a suspension of Dihydropyridine Compound A and hydroxypropylmethyl cellulose in anhydrous ethanol (5 liters) were added lactose and low-substituted hydroxypropyl cellulose, and the resultant mixture was stirred and then the organic solvent was removed under reduced pressure to give solid dispersion composition. After this composition was converted into granules by a conventional method, the granules were further converted with magnesium stearate into tablets by a conventional method, each of which contains 2 mg of Dihydropyridine Compound A.

EXAMPLE 4

For each tablet obtained in Example 3, the coating layer consisting of hydroxypropylmethyl cellulose (5.1 mg), titanium dioxide (1.6 mg), polyethylene glycol- 6000 (0.8 mg), talc (0.4 mg) and iron oxide yellow (0.1 mg) was film-coated by a conventional method to give a film-coated tablet containing 2 mg of Dihydropyridine Compound A.

What we claim is:

1. A method for the treatment of arteriosclerosis in mammals, which comprises administering a dihydropyridine compound of the formula:

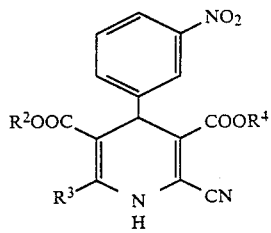

in which $R^2$, $R^3$ and $R^4$ are each $C_1$–$C_4$ alkyl, or a pharmaceutically acceptable salt thereof, to said mammal in need of treatment in an effective antiarteriosclerotic dosage of 0.01–20 mg/kg single dose to a level of 0.5–1000 mg daily dose.

2. A method for the treatment of arteriosclerosis in mammals, which comprises administering the isopropyl ester of 6-cyano-5-methoxycarbonyl-2-methyl-4-(3-nitrophenyl)-1, 4-dihydropyridine-3-carboxylic acid, or a pharmaceutically acceptable salt thereof, to said mammal in need of treatment in an effective anti-arteriosclerotic dosage of 0.01–20 mg/kg single dose to a level of 0.5–1000 mg daily dose.

* * * * *